US008273350B2

(12) United States Patent
Gram et al.

(10) Patent No.: US 8,273,350 B2
(45) Date of Patent: *Sep. 25, 2012

(54) ANTIBODIES TO HUMAN IL-1β

(75) Inventors: Hermann Gram, Weil am Rhein (DE); Franco E Di Padova, Birsfelden (CH)

(73) Assignee: Novartis AG, Basel (CH)

(*) Notice: Subject to any disclaimer, the term of this patent is extended or adjusted under 35 U.S.C. 154(b) by 0 days.

This patent is subject to a terminal disclaimer.

(21) Appl. No.: 13/171,631

(22) Filed: Jun. 29, 2011

(65) Prior Publication Data

US 2011/0256151 A1    Oct. 20, 2011

Related U.S. Application Data

(62) Division of application No. 12/238,502, filed on Sep. 26, 2008, now Pat. No. 7,993,878, which is a division of application No. 10/362,082, filed as application No. PCT/EP01/09588 on Aug. 20, 2001, now Pat. No. 7,446,175.

(30) Foreign Application Priority Data

Aug. 22, 2000 (GB) .................................. 0020685.4

(51) Int. Cl.
*A61K 39/395* (2006.01)
*A61K 39/00* (2006.01)
*C07K 16/24* (2006.01)
*C07K 16/00* (2006.01)
*C12P 21/08* (2006.01)

(52) U.S. Cl. ............... 424/130.1; 424/133.1; 424/141.1; 424/145.1; 530/387.1; 530/387.3; 530/388.1; 530/388.15; 530/388.23

(58) Field of Classification Search .................. None
See application file for complete search history.

(56) References Cited

U.S. PATENT DOCUMENTS

| 4,935,343 | A  | 6/1990  | Allison et al.  |
|-----------|----|---------|-----------------|
| 5,348,858 | A  | 9/1994  | Uetsuki et al.  |
| 5,470,578 | A  | 11/1995 | Aoki et al.     |
| 5,545,806 | A  | 8/1996  | Lonberg et al.  |
| 5,569,825 | A  | 10/1996 | Lonberg et al.  |
| 5,625,126 | A  | 4/1997  | Lonberg et al.  |
| 5,633,425 | A  | 5/1997  | Lonberg et al.  |
| 5,661,016 | A  | 8/1997  | Lonberg et al.  |
| 5,770,429 | A  | 6/1998  | Lonberg et al.  |
| 6,309,636 | B1 | 10/2001 | do Couto et al. |
| 6,632,927 | B2 | 10/2003 | Adair et al.    |

FOREIGN PATENT DOCUMENTS

| EP | 218531     | 4/1987  |
|----|------------|---------|
| EP | 0 267 611  | 5/1988  |
| EP | 0 364 778  | 4/1990  |
| EP | 0 403 1560 | 12/1990 |
| EP | 0 256 055  | 8/1991  |
| EP | 0 323 997  | 4/1993  |
| EP | 0 338 841  | 3/1995  |
| EP | 0 438 474  | 5/1996  |
| EP | 049103     | 5/1996  |
| EP | 0 463 151  | 6/1996  |
| EP | 0 546 073  | 9/1997  |
| WO | WO 88/01649| 3/1988  |
| WO | WO 90/06371| 6/1990  |
| WO | WO 90/07861| 7/1990  |
| WO | WO 91/09968| 7/1991  |
| WO | WO 92/01059| 1/1992  |
| WO | WO 91/09967| 7/1992  |
| WO | WO 95/01197| 1/1995  |
| WO | WO 95/01997| 1/1995  |
| WO | WO 99/42075| 8/1999  |
| WO | WO 01/53353| 7/2001  |

OTHER PUBLICATIONS

Jackson et al., "In Vitro Antibody Maturation-Improvement of a High Affinity, Neutralizing Antibody Against IL-1β", Journal of Immunology, vol. 154, No. 7, pp. 3310-3319, (1995). [XP-000941315].
International Search Report (Apr. 10, 2002).
British Search Report 24 (Jan. 2001).
Straubinger et al., "Two Unusual Human Immunoglobulin V Kappa Genes", Biol Chem, Hoppe-Seyler 369, vol. 7, pp. 601-607, (1988).
Massone et al., "Mapping of Biologically Relevant Sites on Human IL-1β Using Monoclonal Antibodies", The Journal of Immunology, vol. 140, No. 11, pp. 3812-3816, (1988).
Ward et al, "Binding Activities of a Repertoire of Single Immunoglobulin Variable Domains Secreted From *Escherichia coli*", Nature, vol. 341, pp. 544-546, (1989).
Muyldermans et al., "Recognition of Antigens by Single-Domain Antibody Fragments: The Superfluous Luxury of Paired Domains", Trends in Biochemical Sciences, vol. 26, No. 4, pp. 230-235, (2001).
Van den Beucken et al., "Building Novel Binding Ligands to B7.1 and B7.2 Based on Human Antibody Single Variable Light Chain Domains", J. Mol. Biol., vol. 310, pp. 591-601, (2001).
Cacia et al., Biochemistry, 1996, vol. 35, pp. 1897-1903.
Rudikoff et al., Proc. Natl. Acad. Sci, USA, 1982, vol. 79: 1979-1983.
Alberts et al., The Cell, Garland Science, 4th edition, esp. pp. 161, Fig. 3-42, (2002).
Boraschi et al., "Differential Inhibition of IL-1β Activities and Receptor Binding by Monoclonal Antibodies Mapping Within a Discrete Region of the Protein", Lymphokine Research, vol. 10, No. 5, pp. 377-384, (1991).
Herzbeck et al., "Functional and Molecular Characterization of a Monoclonal Antibody against the 165-186 Peptide of Human IL-1β", Scand. J. Immunol. vol. 30, pp. 549-562, (1989).
D'Ettorre et al., "Functional epitope mapping of human interleukin-1β by surface plasmon resonance", Eur. Cytokine Netw., vol. 8, No. 2, pp. 161-171, (1997).
Wu et al., J. Mol. Biol., vol. 294(1):151-162, (1999).

(Continued)

*Primary Examiner* — Xiaozhen Xie
(74) *Attorney, Agent, or Firm* — Leslie Fischer

(57) ABSTRACT

An IL-1β binding molecule, in particular an antibody to human IL-1β, especially a human antibody to human IL-1β is provided, wherein the CDRs of the heavy and light chains have amino acid sequences as defined, for use in the treatment of an IL-1 mediated disease or disorder, e.g. osteoarthritis, osteoporosis and other inflammatory arthritides.

14 Claims, 2 Drawing Sheets

OTHER PUBLICATIONS

Roth R.I., J. Am. Pharm. Assoc. (Wash.), May-Jun., vol. 41(3):383-391, (2001).
Eck, S. L. and Wilson, J. M., 1996, in: Goodman & Gilman's The Pharmacological Basis of Therapeutics, Ninth Edition, McGraw-Hill, New York.
Portolano et al., J. Immunol., vol. 150(3):880-887, (1993).
Clackson et al., Nature, vol. 351:624-628, (1991).
Knappik et al., J. Mol. Biol., vol. 296(1):57-86, (2000).
Rudikoff et al., Proc. Natl. Acad. Sci. USA, 1982, vol. 79:1979-1983.
Wang Z et al., "Humanization of a mouse monoclonal antibody neutralizing TNF-α by guided selection", Journal of Immunological Methods, vol. 241, pp. 171-184, (2000).
Queen, C et al., "A humanized antibody that binds to the interleukin 2 receptor", Proc. Natl. Acad. Sci., vol. 86, pp. 10029-10033, (1989).
Rader C et al., "A phage display approach for rapid antibody humanization: Designed combinatorial V gene libraries", Proc. Natl. Acad. Sci., vol. 95, pp. 8910-8915, (1998).
Davies S et al., "Engineering Mammalian Cells for Recombinant Monoclonal Antibody Production", Department of Chemical and Process Engineering, University of Sheffield, pp. 153-173, (2009).
Riechmann L et al.,"Reshaping human antibodies for therapy", Nature, vol. 332, pp. 323-327, (1988).
Sauder, D.N. "Interleukin 1", Archives of Dermatology, vol. 125, McMaster University, Department of Medicine, Division of Dermatology, Hamilton, Canada, pp. 679-682, May (1989).
Bellini AV, et al., "Production processes of recombinant. IL-1beta from *Bacillus subtilis*: comparison between intracellular and exocellular expression", Journal of Biotechnology, vol. 18, pp. 177-192, (1991).
Feldman et al.,"Anti-TNFalpha Therapy Is Useful in Rheumatoid Arthritis and Crohn's Disease: Analysis of the Mechanism of Action Predicts Utility in Other Diseases", Transplant. Proc., vol. 30, Diseases, Transplant. Proc., vol. 30, pp. 4126-4127, 1998 pp. 4126-4127, (1998).
Cochlovius et al., Therapeutics Antibodies—After Years of promise, magic bullets appear to be on the upswing, Modern Drug Discover, pp. 33-38, (2003).
Van Noort et al., "Cell Biology of Autoimmune Diseases", International Review of Cytology, vol. 178, pp. 127-204, Table III in particular, (1998).
Mestas et al., "Of Mice and Not Men: Differences between Mouse and Human Immunology", J. of Immunology, vol. 172, pp. 2731-2738, (2004).
Bioinformatics Software, "Chimera", available at :http:/www.cgl.ucsf.edu/chimera, printed on Mar. 18, 2011.
Paul, William E, Fundamental Immunology, 4th Ed., Chapter 3 "Immunoglobulins: Structure and Function", Lippencott-Raven Publishers, pp. 37-74 (in particular pp. 37, 43, 58, 59), (1999).
Borrebaeck et al., "Kinetic Analysis of Recombinant Antibody-Antigen Interactions: Relation Between Structural Domains and Antigen Binding", Nature, vol. 10 (6), pp. 697-698, (1992).
Matsuda F. et al., Journal of Experimental Medicine, vol. 188 (11) pp. 2151-2162, (1998).
Philip L. Simon et al., "Mapping of Neutralizing Epitopes and the Receptor Bindng Site of Human Interleukin 1 β", J. bio. Chem., vol. 268, No. 13, pp. 9771-9779, (1993).
Reiter et al., J. Mol. Biol. vol. 290, pp. 685-698, (1999).
Riechmann, Muyldermans, "Single domain antibodies: comparison of camel VH and camelised human VH domains", Journal of Immu. Methods, vol. 231, pp. 25-38, (1999).
Bigio et al., "One-step immunoaffinity purification of bioactive human recombinant IL-1 β with a monoclonal antibody directed to a well-exposed domain of the protein", Journal of Immunological Methods, vol. 123, pp. 1-8. (1989).
Pascalis et al., "Grafting of "Abbreviated" Complementarity—Determining Regions Containing Specificity—Determining Residues Essential for Ligan Contact to Engineer a Less Immunogenic Humanized Monoclonal Antibody", The Journal of Immunology, vol. 169, pp. 3076-3084, (2002).
Panka et al., "Variable region framework differences result in decreased or increased affinity of variant anti-gigoxin antibodies", Proc Natl. Acad Sci USA, vol. 85, pp. 3080-3084, (1988).
Colman et al., "Effects of amino acid sequence changes on antibody-antigen interactions", Research in Immmunology, vol. 145(1), pp. 33-36, (1994).
Abaza et al., J. of Protein Chem., vol. 11 (5), pp. 433-444, (1992).

Figure 2

ACZ885 Heavy chain variable region

```
     ATGGAGTTTGGGCTGAGCTGGGTTTTCCTCGTTGCTCTTTTAAGAGGTGTCCAGTGTCAG
-19   M  E  F  G  L  S  W  V  F  L  V  A  L  L  R  G  V  Q  C  Q    + 1

GTGCAGCTGGTGGAGTCTGGGGGAGGCGTGGTCCAGCCTGGGAGGTCCCTGAGACTCTCC
      V  Q  L  V  E  S  G  G  G  V  V  Q  P  G  R  S  L  R  L  S   + 21

TGTGCAGCGTCTGGATTCACCTTCAGTGTTTATGGCATGAACTGGGTCCGCCAGGCTCCA
      C  A  A  S  G  F  T  F  S  V  Y  G  M  N  W  V  R  Q  A  P   + 41

GGCAAGGGGCTGGAGTGGGTGGCAATTATTTGGTATGATGGAGATAATCAATACTATGCA
      G  K  G  L  E  W  V  A  I  I  W  Y  D  G  D  N  Q  Y  Y  A   + 61

GACTCCGTGAAGGGCCGATTCACCATCTCCAGAGACAATTCCAAGAACACGCTGTATCTG
      D  S  V  K  G  R  F  T  I  S  R  D  N  S  K  N  T  L  Y  L   + 81

CAAATGAACGGCCTGAGAGCCGAGGACACGGCTGTGTATTATTGTGCGAGAGATCTTAGG
      Q  M  N  G  L  R  A  E  D  T  A  V  Y  Y  C  A  R  D  L  R  + 101

ACTGGGCCTTTTGACTACTGGGGCCAGGGAACCCTGGTCACCGTCTCCTC
      T  G  P  F  D  Y  W  G  Q  G  T  L  V  T  V  S  S           + 118
```

ACZ885 Light chain variable region

```
      ATGTTGCCATCACAACTCATTGGGTTTCTGCTGCTCTGGGTTCCAGCCTCCAGGGGTGAA
-19   M  L  P  S  Q  L  I  G  F  L  L  L  W  V  P  A  S  R  G  E   + 1

ATTGTGCTGACTCAGTCTCCAGACTTTCAGTCTGTGACTCCAAAGGAGAAAGTCACCATC
       I  V  L  T  Q  S  P  D  F  Q  S  V  T  P  K  E  K  V  T  I  + 21

ACCTGCCGGGCCAGTCAGAGCATTGGTAGTAGCTTACACTGGTACCAGCAGAAACCAGAT
       T  C  R  A  S  Q  S  I  G  S  S  L  H  W  Y  Q  Q  K  P  D  + 41

CAGTCTCCAAAGCTCCTCATCAAGTATGCTTCCCAGTCCTTCTCAGGGGTCCCCTCGAGG
       Q  S  P  K  L  L  I  K  Y  A  S  Q  S  F  S  G  V  P  S  R  + 61

TTCAGTGGCAGTGGATCTGGGACAGATTTCACCCTCACCATCAATAGCCTGGAAGCTGAA
       F  S  G  S  G  S  G  T  D  F  T  L  T  I  N  S  L  E  A  E  + 81

GATGCTGCAGCGTATTACTGTCATCAGAGTAGTAGTTTACCATTCACTTTCGGCCCTGGG
       D  A  A  A  Y  Y  C  H  Q  S  S  S  L  P  F  T  F  G  P  G + 101

ACCAAAGTGGATATCAAA                                            + 107
       T  K  V  D  I  K
```

ANTIBODIES TO HUMAN IL-1β

This is a divisional of application Ser. No. 12/238,502, filed Sep. 26, 2008, which issued as U.S. Pat. No. 7,993,878, which is a divisional of application Ser. No. 10/362,082 filed on Oct. 15, 2003, which issued as U.S. Pat. No. 7,446,175, which is 371 of International Application No. PCT/EP01/09588 filed on Aug. 20, 2001, which claims benefit of Great Britain Application No. 0020685.4 filed on Aug. 22, 2000, the entire disclosures of which are hereby incorporated by reference.

FIELD OF THE DISCLOSURE

This invention relates to antibodies to human interleukin I beta (IL-1β) and to the use of such antibodies for the treatment of IL-1 mediated diseases and disorders.

BACKGROUND OF THE DISCLOSURE

Interleukin 1 (IL-1) is an activity produced by cells of the immune system which acts as a mediator of the acute phase inflammatory response. Inappropriate or excessive production of IL-1, in particular IL-1β, is associated with the pathology of various diseases and disorders, such as septicemia, septic or endotoxic shock, allergies, asthma, bone loss, ischemia, stroke, rheumatoid arthritis and other inflammatory disorders. Antibodies to IL-1β have been proposed for use in the treatment of IL-1 mediated diseases and disorders; see for instance, WO 95/01997 and the discussion in the introduction thereof.

We have now prepared improved antibodies to human IL-1β for use in the treatment of IL-1 mediated diseases and disorders.

SUMMARY OF THE DISCLOSURE

Accordingly the invention provides an IL-1β binding molecule which comprises an antigen binding site comprising at least one immunoglobulin heavy chain variable domain ($V_H$) which comprises in sequence hypervariable regions CDR1, CDR2 and CDR3, said CDR1 having the amino acid sequence Val-Tyr-Gly-Met-Asn (SEQ ID NO:5), said CDR2 having the amino acid sequence Ile-Ile-Trp-Tyr-Asp-Gly-Asp-Asn-Gln-Tyr-Tyr-Ala-Asp-Ser-Val-Lys-Gly (SEQ ID NO:6), and said CDR3 having the amino acid sequence Asp-Leu-Arg-Thr-Gly-Pro (SEQ ID NO:7); and direct equivalents thereof.

Accordingly the invention also provides an IL-1β binding molecule comprising at least one immunoglobulin light chain variable domain ($V_L$) which comprises in sequence hypervariable regions CDR1', CDR2' and CDR3', said CDR1' having the amino acid sequence Arg-Ala-Ser-Gln-Ser-Ile-Gly-Ser-Ser-Leu-His (SEQ ID NO:8) said CDR2' having the amino acid sequence Ala-Ser-Gln-Ser-Phe-Ser (SEQ ID NO:9) and said CDR3' having the amino acid sequence His-Gln-Ser-Ser-Ser-Leu-Pro (SEQ ID NO:10) and direct equivalent thereof.

In a first aspect the invention provides a single domain IL-1β binding molecule comprising an isolated immunoglobulin heavy chain comprising a heavy chain variable domain ($V_H$) as defined above.

In a second aspect the invention also provides an IL-1β binding molecule comprising both heavy ($V_H$) and light chain ($V_L$) variable domains in which said IL-1β binding molecule comprises at least one antigen binding site comprising:

a) an immunoglobulin heavy chain variable domain ($V_H$) which comprises in sequence hypervariable regions CDR1, CDR2 and CDR3, said CDR1 having the amino acid sequence Val-Tyr-Gly-Met-Asn (SEQ ID NO:5), said CDR2 having the amino acid sequence Ile-Ile-Trp-Tyr-Asp-Gly-Asp-Asn-Gln-Tyr-Tyr-Ala-Asp-Ser-Val-Lys-Gly (SEQ ID NO:6), and said CDR3 having the amino acid sequence Asp-Leu-Arg-Thr-Gly-Pro (SEQ ID NO:7), and b) an immunoglobulin light chain variable domain ($V_L$) which comprises in sequence hypervariable regions CDR1', CDR2' and CDR3', said CDR1' having the amino acid sequence Arg-Ala-Ser-Gln-Ser-Ile-Gly-Ser-Ser-Leu-His (SEQ ID NO:8), said CDR2' having the amino acid sequence Ala-Ser-Gln-Ser-Phe-Ser (SEQ ID NO:9), and said CDR3' having the amino acid sequence His-Gln-Ser-Ser-Ser-Leu-Pro (SEQ ID NO:10);

and direct equivalents thereof.

BRIEF DESCRIPTION OF THE FIGURE

FIG. 2 provides the variable heavy and light chain regions of the ACZ885 antibody. The top portion displays the heavy chain, and shows the 19 amino acid leader sequence (italics) and the CDRs (bold). The bottom portion displays the light chain, and shows the 19 amino acid leader sequence (italics) and the CDRs (bold).

DETAILED DESCRIPTION OF THE DISCLOSURE

Figure 1:
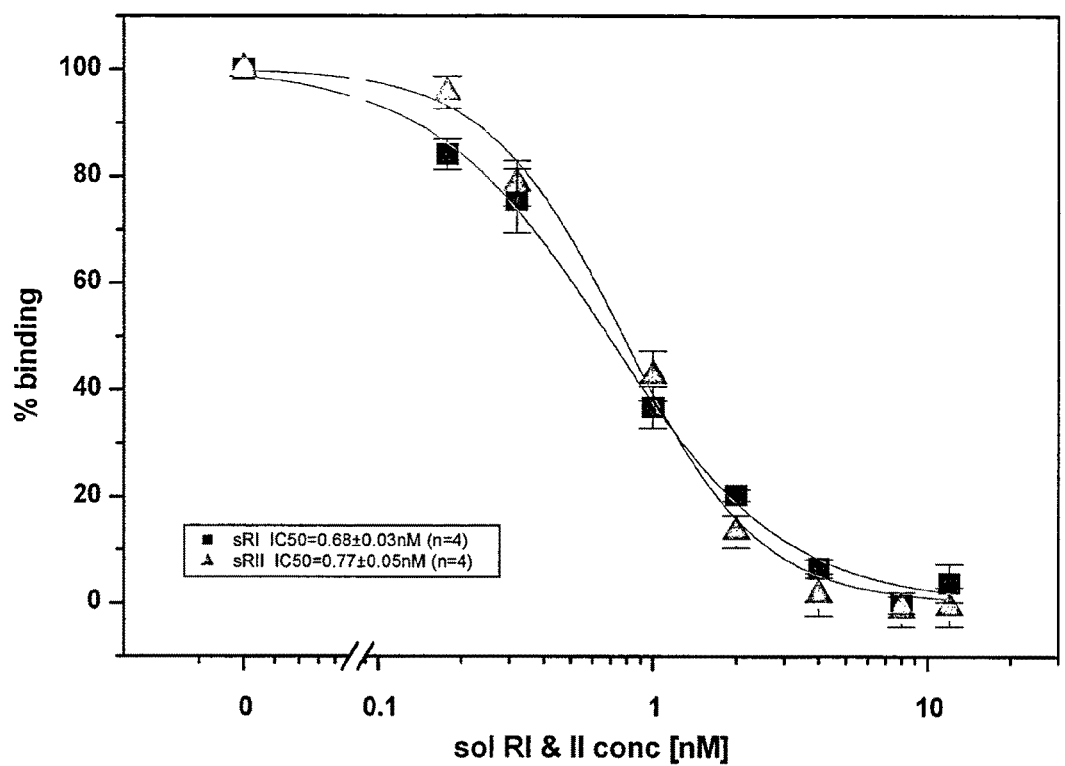
FIG. 1 shows dose response curves for the inhibition of IL-1b binding by soluble IL-1 receptors I and II.

Unless otherwise indicated, any polypeptide chain is herein described as having an amino acid sequence starting at the N-terminal extremity and ending at the C-terminal extremity. When the antigen binding site comprises both the $V_H$ and $V_L$ domains, these may be located on the same polypeptide molecule or, preferably, each domain may be on a different chain, the $V_H$ domain being part of an immunoglobulin heavy chain or fragment thereof and the $V_L$ being part of an immunoglobulin light chain or fragment thereof.

By "IL-1β binding molecule" is meant any molecule capable of binding to the IL-1β antigen either alone or associated with other molecules. The binding reaction may be shown by standard methods (qualitative assays) including, for example, a bioassay for determining the inhibition of IL-1β binding to its receptor or any kind of binding assays, with reference to a negative control test in which an antibody of unrelated specificity but of the same isotype, e.g. an anti-CD25 antibody, is used. Advantageously, the binding of the IL-1β binding molecules of the invention to IL-1β may be shown in a competitive binding assay.

Examples of antigen binding molecules include antibodies as produced by B-cells or hybridomas and chimeric, CDR-grafted or human antibodies or any fragment thereof, e.g. F(ab')$_2$ and Fab fragments, as well as single chain or single domain antibodies.

A single chain antibody consists of the variable domains of the heavy and light chains of an antibody covalently bound by a peptide linker usually consisting of from 10 to 30 amino acids, preferably from 15 to 25 amino acids. Therefore, such a structure does not include the constant part of the heavy and light chains and it is believed that the small peptide spacer should be less antigenic than a whole constant part. By "chimeric antibody" is meant an antibody in which the constant regions of heavy or light chains or both are of human origin while the variable domains of both heavy and light chains are of non-human (e.g., murine) origin or of human origin but derived from a different human antibody. By "CDR-grafted antibody" is meant an antibody in which the hypervariable regions (CDRs) are derived from a donor antibody, such as a non-human (e.g. murine) antibody or a different human antibody, while all or substantially all the other parts of the immunoglobulin e.g. the constant regions and the highly conserved parts of the variable domains, i.e. the framework regions, are derived from an acceptor antibody, e.g. an antibody of human origin. A CDR-grafted antibody may however contain a few amino acids of the donor sequence in the framework regions, for instance in the parts of the framework regions adjacent to the hypervariable regions. By "human antibody" is meant an antibody in which the constant and variable regions of both the heavy and light chains are all of human origin, or substantially identical to sequences of human origin, not necessarily from the same antibody and includes antibodies produced by mice in which the murine immunoglobulin variable and constant part genes have been replaced by their human counterparts, e.g. as described in general terms in EP 0546073 B1, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP 0 438474 B1 and EP 0 463151 B1.

Particularly preferred IL-1β binding molecules of the invention are human antibodies especially the ACZ 885 antibody as hereinafter described in the Examples.

Thus in preferred chimeric antibodies the variable domains of both heavy and light chains are of human origin, for instance those of the ACZ 885 antibody which are shown in SEQ ID NO:1 and SEQ ID NO:2. The constant region domains preferably also comprise suitable human constant region domains, for instance as described in "Sequences of Proteins of Immunological Interest", Kabat E. A. et al, US Department of Health and Human Services, Public Health Service, National Institute of Health Hypervariable regions may be associated with any kind of framework regions, though preferably are of human origin. Suitable framework regions are described in Kabat E. A. et al, ibid. The preferred heavy chain framework is a human heavy chain framework, for instance that of the ACZ 885 antibody which is shown in SEQ ID NO:1. It consists in sequence of FR1, FR2, FR3 and FR4 regions. In a similar manner, SEQ ID NO:2 shows the preferred ACZ 885 light chain framework which consists, in sequence, of FR1', FR2', FR3' and FR4' regions.

Accordingly, the invention also provides an IL-1β binding molecule which comprises at least one antigen binding site comprising either a first domain having an amino acid sequence substantially identical to that shown in SEQ ID NO:1 starting with the amino acid at position 20 and ending with the amino acid at position 137 or a first domain as described above and a second domain having an amino acid sequence substantially identical to that shown in SEQ ID NO:2, starting with the amino acid at position 20 and ending with the amino acid at position 126.

Monoclonal antibodies raised against a protein naturally found in all humans are typically developed in a non-human system e.g. in mice, and as such are typically non-human proteins. As a direct consequence of this, a xenogenic antibody as produced by a hybridoma, when administered to humans, elicits an undesirable immune response which is predominantly mediated by the constant part of the xenogenic immunoglobulin. This clearly limits the use of such antibodies as they cannot be administered over a prolonged period of time. Therefore it is particularly preferred to use single chain, single domain, chimeric, CDR-grafted, or especially human antibodies which are not likely to elicit a substantial allogenic response when administered to humans.

In view of the foregoing, a more preferred IL-1β binding molecule of the invention is selected from a human anti IL-1β antibody which comprises at least
  a) an immunoglobulin heavy chain or fragment thereof which comprises (i) a variable domain comprising in sequence the hypervariable regions CDR1, CDR2 and CDR3 and (ii) the constant part or fragment thereof of a human heavy chain; said CDR1 having the amino acid sequence Val-Tyr-Gly-Met-Asn (SEQ ID NO:5), said CDR2 having the amino acid sequence Ile-Ile-Trp-Tyr-Asp-Gly-Asp-Asn-Gln-Tyr-Tyr-Ala-Asp-Ser-Val-Lys-Gly (SEQ ID NO:6), and said CDR3 having the amino acid sequence Asp-Leu-Arg-Thr-Gly-Pro (SEQ ID NO:7) and
  b) an immunoglobulin light chain or fragment thereof which comprises (i) a variable domain comprising in sequence the hypervariable regions and optionally also the CDR1', CDR2', and CDR3' hypervariable regions and (ii) the constant part or fragment thereof of a human light chain, said CDR1' having the amino acid sequence Arg-Ala-Ser-Gln-Ser-Ile-Gly-Ser-Ser-Leu-His (SEQ ID NO:8), said CDR2' having the amino acid sequence Ala-Ser-Gln-Ser-Phe-Ser (SEQ ID NO:9), and said CDR3' having the amino acid sequence His-Gln-Ser-Ser-Ser-Leu-Pro (SEQ ID NO:10);
and direct equivalents thereof.

Alternatively, an IL-1β binding molecule of the invention may be selected from a single chain binding molecule which comprises an antigen binding site comprising
  a) a first domain comprising in sequence the hypervariable regions CDR1, CDR2 and CDR3, said hypervariable regions having the amino acid sequences as shown in SEQ ID NO:1,
  b) A second domain comprising the hypervariable regions CDR1', CDR2' and CDR3' said hypervariable regions having the amino acid sequences as shown in SEQ ID NO:2 and
  c) a peptide linker which is bound either to the N-terminal extremity of the first domain and to the C-terminal extremity of the second domain or to the C-terminal extremity of the first domain and to the N-terminal extremity of second domain;
and direct equivalents thereof.

As it is well known, minor changes in an amino acid sequence such as deletion, addition or substitution of one, a few or even several amino acids may lead to an allelic form of the original protein which has substantially identical properties.

Thus, by the term "direct equivalents thereof" is meant either any single domain IL-1β binding molecule (molecule X).
(i) in which the hypervariable regions CDR1, CDR2 and CDR3 taken as a whole are at least 80% homologous, preferably at least 90% homologous, more preferably at least 95% homologous to the hypervariable regions as shown in SEQ ID NO:1 and,
(ii) which is capable of inhibiting the binding of IL-1β to its receptor substantially to the same extent as a reference molecule having framework regions identical to those of molecule X but having hypervariable regions CDR1, CDR2 and CDR3 identical to those shown in SEQ ID NO:1
or any IL-1β binding molecule having at least two domains per binding site (molecule X')
(i) in which the hypervariable regions CDR1, CDR2, CDR3, CDR1', CDR2' and CDR3' taken as a whole are at least 80% homologous, preferably at least 90% homologous, more preferably at least 95% homologous, to the hypervariable regions as shown in SEQ ID NO:1 and 2 and (ii) which is capable of inhibiting the binding of IL-1β to its receptor substantially to the same extent as a reference molecule having framework regions and constant parts identical to molecule X', but having hypervariable regions CDR1, CDR2, CDR3, CDR1', CDR2' and CDR3', identical to those shown in SEQ ID NO:1 and 2.

In the present description amino acid sequences are at least 80% homologous to one another if they have at least 80% identical amino acid residues in a like position when the sequence are aligned optimally, gaps or insertions in the amino acid sequences being counted as non-identical residues.

The inhibition of the binding of IL-1β to its receptor may be conveniently tested in various assays including such assays are described hereinafter in the text. By the term "to the same extent" is meant that the reference and the equivalent molecules exhibit, on a statistical basis, essentially identical IL-1β binding inhibition curves in one of the assays referred to above. For example, in IL-1β binding molecules of the invention typically have $IC_{50}$s for the inhibition of the binding of IL-1β to its receptor which are within +/−x5 of that of, preferably substantially the same as, the $IC_{50}$ of the corresponding reference molecule when assayed as described above.

For example, the assay used may be an assay of competitive inhibition of binding of IL-1β by soluble IL-1 receptors and the IL-1β binding molecules of the invention.

Most preferably, the human IL-1β antibody comprises at least a) one heavy chain which comprises a variable domain having an amino acid sequence substantially identical to that shown in SEQ ID NO:1 starting with the amino acid at position 20 and ending with the amino acid at position 137 and the constant part of a human heavy chain; and b) one light chain which comprises a variable domain having an amino acid sequence substantially identical to that shown in SEQ ID NO:2 starting with the amino acid at position 20 and ending with the amino acid at position 126 and the constant part of a human light chain.

The constant part of a human heavy chain may be of the $\gamma_1$, $\gamma_2$, $\gamma_3$, $\gamma_4$, μ, $\alpha_1$, $\alpha_2$, δ or ε type, preferably of the γ type, more preferably of the $\gamma_1$ type, whereas the constant part of a human light chain may be of the κ or λ type (which includes the $\lambda_1$, $\lambda_2$ and $\lambda_3$ subtypes) but is preferably of the κ type. The amino acid sequences of all these constant parts are given in Kabat et al ibid.

An IL-1β binding molecule of the invention may be produced by recombinant DNA techniques. In view of this, one or more DNA molecules encoding the binding molecule must be constructed, placed under appropriate control sequences and transferred into a suitable host organism for expression.

In a very general manner, there are accordingly provided (i) DNA molecules encoding a single domain IL-1β binding molecule, of the invention, a single chain IL-1β binding molecule of the invention, a heavy or light chain or fragments thereof of a IL-1β binding molecule of the invention and (ii) the use of the DNA molecules of the invention for the production of a IL-1β binding molecule of the invention by recombinant means.

The present state of the art is such that the skilled worker in the art is able to synthesize the DNA molecules of the invention given the information provided herein i.e. the amino acid sequences of the hypervariable regions and the DNA sequences coding for them. A method for constructing a variable domain gene is for example described in EPA 239 400 and may be briefly summarized as follows: A gene encoding a variable domain of a MAb of whatever specificity is cloned. The DNA segments encoding the framework and hypervariable regions are determined and the DNA segments encoding the hypervariable regions are removed so that the DNA segments encoding the framework regions are fused together with suitable restriction sites at the junctions. The restriction sites may be generated at the appropriate positions by mutagenesis of the DNA molecule by standard procedures. Double stranded synthetic CDR cassettes are prepared by DNA synthesis according to the sequences given in SEQ ID NO:1 or 2. These cassettes are provided with sticky ends so that they can be ligated at the junctions of the framework Furthermore, it is not necessary to have access to the mRNA from a producing hybridoma cell line in order to obtain a DNA construct coding for the IL-1β binding molecules of the invention. Thus PCT application WO 90/07861 gives full instructions for the production of an antibody by recombinant DNA techniques given only written information as to the nucleotide sequence of the gene. The method comprises the synthesis of a number of oligonucleotides, their amplification by the PCR method, and their splicing to give the desired DNA sequence.

Expression vectors comprising a suitable promoter or genes encoding heavy and light chain constant parts are publicly available. Thus, once a DNA molecule of the invention is prepared it may be conveniently transferred in an appropriate expression vector. DNA molecules encoding single chain antibodies may also be prepared by standard methods, for example, as described in WO 88/1649.

In view of the foregoing no hybridoma or cell line deposit is necessary to comply with the criteria of sufficiency of description.

In a particular embodiment the invention includes first and second DNA constructs for the production of an IL-1β binding molecule as described below:

The first DNA construct encodes a heavy chain or fragment thereof and comprises a) a first part which encodes a variable domain comprising alternatively framework and hypervariable regions, said hypervariable regions being in sequence CDR1, CDR2 and CDR3 the amino acid sequences of which are shown in SEQ ID NO:1; this first part starting with a codon encoding the first amino acid of the variable domain and ending with a codon encoding the last amino acid of the variable domain, and b) a second part encoding a heavy chain constant part or fragment thereof which starts with a codon encoding the first amino acid of the constant part of the heavy chain and ends with a codon encoding the last amino acid of the constant part or fragment thereof, followed by a stop codon.

Preferably, this first part encodes a variable domain having an amino acid sequence substantially identical to the amino acid sequence as shown in SEQ ID NO:1 starting with the amino acid at position 20 and ending with the amino acid at position 137. More preferably the first part has the nucleotide sequence as shown in SEQ ID NO:3 starting with the nucleotide at position 58 and ending with the nucleotide at position 410. Also preferably, the second part encodes the constant part of a human heavy chain, more preferably the constant part of the human γ1 chain. This second part may be a DNA fragment of genomic origin (comprising introns) or a cDNA fragment (without introns).

The second DNA construct encodes a light chain or fragment thereof and comprises
  a) a first part which encodes a variable domain comprising alternatively framework and hypervariable regions; said hypervariable regions being CDR3' and optionally CDR1' and CDR2', the amino acid sequences of which are shown in SEQ ID NO:2; this first part starting with a codon encoding the first amino acid of the variable domain and ending with a codon encoding the last amino acid of the variable domain, and
  b) a second part encoding a light chain constant part or fragment thereof which starts with a codon encoding the first amino acid of the constant part of the light chain and ends with a codon encoding the last amino acid of the constant part or fragment thereof followed by a stop codon.

Preferably, this first part encodes a variable domain having an amino acid sequence substantially identical to the amino acid sequence as shown in SEQ ID NO:2 starting with the amino acid at position 20 and ending with the amino acid at position 126. More preferably, the first part has the nucleotide sequence as shown in SEQ ID NO:4 starting with the nucleotide at position 58 and ending with the nucleotide at position 378. Also preferably the second part encodes the constant part of a human light chain, more preferably the constant part of the human κ chain.

The invention also includes IL-1β binding molecules in which one or more of the residues of CDR1, CDR2, CDR3, CDR1', CDR2' or CDR3' or the frameworks, typically only a few (e.g. 1-4), are changed from the residues shown in SEQ ID NO:1 and SEQ ID NO:2, for instance by mutation e.g. site directed mutagenesis of the corresponding DNA sequences. The invention includes the DNA sequences coding for such changed IL-1β binding molecules. In particular the invention includes IL-1β binding molecules in which one or more residues of CDR1' or CDR2' have been changed from the residues shown in SEQ ID NO:2.

In the first and second DNA constructs, the first and second parts may be separated by an intron, and, an enhancer may be conveniently located in the intron between the first and second parts. The presence of such an enhancer which is transcribed but not translated, may assist in efficient transcription. In particular embodiments the first and second DNA constructs comprise the enhancer of a heavy chain gene advantageously of human origin.

Each of the DNA constructs are placed under the control of suitable control sequences, in particular under the control of a suitable promoter. Any kind of promoter may be used, provided that it is adapted to the host organism in which the DNA constructs will be transferred for expression. However, if expression is to take place in a mammalian cell, it is particularly preferred to use the promoter of an immunoglobulin gene.

The desired antibody may be produced in a cell culture or in a transgenic animal. A suitable transgenic animal may be obtained according to standard methods which include micro injecting into eggs the first and second DNA constructs placed under suitable control sequences transferring the so prepared eggs into appropriate pseudo-pregnant females and selecting a descendant expressing the desired antibody.

When the antibody chains are produced in a cell culture, the DNA constructs must first be inserted into either a single expression vector or into two separate but compatible expression vectors, the latter possibility being preferred.

Accordingly, the invention also provides an expression vector able to replicate in a prokaryotic or eukaryotic cell line which comprises at least one of the DNA constructs above described.

Each expression vector containing a DNA construct is then transferred into a suitable host organism. When the DNA constructs are separately inserted on two expression vectors, they may be transferred separately, i.e. one type of vector per cell, or co-transferred, this latter possibility being preferred. A suitable host organism may be a bacterium, a yeast or a mammalian cell line, this latter being preferred. More preferably, the mammalian cell line is of lymphoid origin, e.g. a myeloma, hybridoma or a normal immortalised B-cell, which conveniently does not express any endogenous antibody heavy or light chain.

For expression in mammalian cells it is preferred that the IL-1β binding molecule coding sequence is integrated into the host cell DNA within a locus which permits or favours high level expression of the IL-1β binding molecule. Cells in which the IL-1β binding molecule coding sequence is integrated into such favourable loci may be identified and selected on the basis of the levels of the IL-1β binding molecule which they express. Any suitable selectable marker may be used for preparation of host cells containing the IL-1β binding molecule coding sequence; for instance, a dhfr gene/methotrexate or equivalent selection system may be used. Alternative systems for expression of the IL-1β binding molecules of the invention include GS-based amplification/selection systems, such as those described in EP 0256055 B, EP 0323997 B and European patent application 89303964.4.

In a further aspect of the invention there is provided a process for the product of an IL-1β binding molecule which comprises (i) culturing an organism which is transformed with an expression vector as defined above and (ii) recovering the IL-1β binding molecule from the culture.

In accordance with the present invention it has been found that the ACZ 885 antibody appears to have binding specificity for the antigenic epitope of human IL-1β which includes the loop comprising the Glu 64 residue of mature human IL-1β. (Residue Glu 64 of mature human IL-1β correspond to residue 180 of the human IL-1β precursor.) This epitope appears to be outside the recognition site of the IL-1 receptor and it is therefore most surprising that antibodies to this epitope, e.g. the ACZ 885 antibody, are capable of inhibiting the binding of IL-1β to its receptor. Antibodies, in particular chimeric and CDR-grafted antibodies and especially human antibodies, which have binding specificity for the antigenic epitope of mature human IL-1β which includes the loop comprising residue Glu 64 and which are capable of inhibiting the binding of IL-1β to its receptor; and use of such antibodies for the treatment of IL-1 mediated diseases and disorders, are novel and are included within the scope of the present invention.

Thus in a further aspect the invention includes an antibody to IL-1β which has antigen binding specificity for an antigenic epitope of human IL-1β which includes the loop comprising residue Glu 64 of mature human IL-1β and which is capable of inhibiting the binding of IL-1β to its receptor.

In yet further aspects the invention includes:
  i) use of an antibody to IL-1β, which has antigen binding specificity for an antigenic epitope of mature human IL-1β which includes the loop comprising Glu 64 and which is capable of inhibiting the binding of IL-1β to its receptor, for the treatment of an IL-1 mediated disease or disorder;
  ii) a method for the treatment of an IL-1 mediated disease or disorders in a patient which comprises administering to the patient an effective amount of an antibody to IL-1β, which has antigen binding specificity for an antigenic epitope of mature human IL-1β which includes the loop comprising Glu 64 and which is capable of inhibiting the binding of IL-1β to its receptor;

iii) a pharmaceutical composition comprising an antibody to IL-1β, which has antigen binding specificity for an antigenic epitope of mature human IL-1β which includes the loop comprising Glu 64 and which is capable of inhibiting the binding of IL-1β to its receptor, in combination with a pharmaceutically acceptable excipient, diluent or carrier; and iv) use of an antibody to IL-1β, which has antigen binding specificity for an antigenic epitope of mature human IL-1β which includes the loop comprising Glu 64 and which is capable of inhibiting the binding of IL-1β to its receptor, for the preparation of a medicament for the treatment of an IL-1 mediated disease or disorder.

For the purposes of the present description an antibody is "capable of inhibiting the binding of IL-1β" if the antibody is capable of inhibiting the binding of IL-1β to its receptor substantially to the same extent as the ACZ 885 antibody, wherein "to the same extent" has meaning as defined above.

The ACZ 885 antibody has binding affinity for IL-1β which is higher than affinities previously reported for anti-IL-1β antibodies e.g. anti human IL-1β antibodies. Thus ACZ 885 has a dissociation equilibrium constant $K_D$ for binding to IL-1β of less than about 50 pM, e.g. about 35 pM. This high binding affinity makes the ACZ antibody particularly suitable for therapeutic applications.

Thus in a yet further aspect the invention provides an antibody to IL-1β which has a $K_D$ for binding to IL-1β of about 50 pM or less. This aspect of the invention also includes uses methods and compositions for such high affinity antibodies, as described above for antibodies to IL-1β have binding specificity for an antigenic determinant of mature human IL-1β which includes the loop comprising Glu 64.

In the present description the phrase "Il-1 mediated disease" encompasses all diseases and medical conditions in which IL-1 plays a role, whether directly or indirectly, in the disease or medical condition, including the causation, development, progress, persistence or pathology of the disease or condition.

In the present description the terms "treatment" or "treat" refer to both prophylactic or preventative treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse.

IL-1β binding molecules as defined above, in particular IL-1β binding molecules according to the first and second aspects of the invention antibodies which have binding specificity for the antigenic epitope of mature human IL-1β which includes the loop comprising Glu 64, in particular antibodies which are capable of inhibiting the binding of IL-1β to its receptor; and antibodies to IL-1β which have a $K_D$ for binding to IL-1β of about 50 pM or less are herein referred to as Antibodies of the Invention.

Preferably the Antibodies of the Invention are IL-1β binding molecules according to the first and second aspects of the invention. Advantageously the Antibodies of the Invention are human antibodies, most preferably the ACZ 885 antibody or direct equivalent thereof.

The Antibodies of the Invention block the effects of IL-1β on its target cells and thus are indicated for use in the treatment of IL-1 mediated diseases and disorders. These and other pharmacological activities of the Antibodies of the Invention may be demonstrated in standard test methods for example as described below:

Neutralization of IL-1β Dependent Production of $PGE_2$ and Interleukin-6 by Primary Human Fibroblasts The production of $PGE_2$ and IL-6 in primary human dermal fibroblasts is dependent on IL-1β. TNF-α alone cannot efficiently induce these inflammatory mediators, but synergizes with IL-1. Primary dermal fibroblasts are used as a surrogate model for IL-1-induced cellular activation.

Primary human fibroblasts are stimulated with recombinant IL-1β or conditioned medium obtained from LPS-stimulated human PBMCs in the presence of various concentrations of Antibody of the Invention or IL-1RA ranging from 6 to 18,000 pM. The chimeric anti-CD25 antibody SIMULECT® (basiliximab) is used as a matched isotype control. Supernatant is taken after 16 h stimulation and assayed for IL-6 by ELISA. Antibodies of the Invention typically have $IC_{50}$s for inhibition of IL-6 production of about 1 nM or less (e.g. from about 0.1 to about 1 nM) when tested as above.

As indicated in the above assay Antibodies of the Invention potently block the effects of IL-1β. Accordingly, the Antibodies of the Invention have pharmaceutical utility as follows:

Antibodies of the Invention are useful for the prophylaxis and treatment of IL-1 mediated diseases or medical conditions, e.g. inflammatory conditions, allergies and allergic conditions, hypersensitivity reactions, autoimmune diseases, severe infections, and organ or tissue transplant rejection.

For example, Antibodies of the Invention may be use for the treatment of recipients of heart, lung, combined heart-lung, liver, kidney, pancreatic, skin or corneal transplants, including allograft rejection or xenograft rejection, and for the prevention of graft-versus-host disease, such as following bone marrow transplant, and organ transplant associated arteriosclerosis.

Antibodies of the Invention are particularly useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, hypersensitivity (including both airways hypersensitivity and dermal hypersensitivity) and allergies. Specific autoimmune diseases for which Antibodies of the Invention may be employed include autoimmune haematological disorders (including e.g. hemolytic anaemia, aplastic anaemia, pure red cell anaemia and idiopathic thrombocytopenia), systemic lupus erythematosus, polychondritis, sclerodoma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Antibodies of the Invention are also useful for the treatment, prevention, or amelioration of asthma, bronchitis, pneumoconiosis, pulmonary emphysema, and other obstructive or inflammatory diseases of the airways Antibodies of the Invention are useful for treating undesirable acute and hyperacute inflammatory reactions which are mediated by IL-1 or involve IL-1 production, especially IL-1β, or the promotion of TNF release by IL-1, e.g. acute infections, for example septic shock (e.g., endotoxic shock and adult respiratory distress syndrome), meningitis, pneumonia; and severe burns; and for the treatment of cachexia or wasting syndrome associated with morbid TNF release, consequent to infection, cancer, or organ dysfunction, especially AIDS-related cachexia, e.g., associated with or consequential to HIV infection.

Antibodies of the Invention are particularly useful for treating diseases of bone metabolism including osteoarthritis, osteoporosis and other inflammatory arthritides, and bone loss in general, including age-related bone loss, and in particular periodontal disease.

For these indications, the appropriate dosage will, of course, vary depending upon, for example, the particular Antibody of the Invention to be employed, the host, the mode of administration and the nature and severity of the condition being treated. However, in prophylactic use, satisfactory results are generally indicated to be obtained at dosages from about 0.05 mg to about 10 mg per kilogram body weight more usually from about 0.1 mg to about 5 mg per kilogram body weight. The frequency of dosing for prophylactic uses will normally be in the range from about once per week up to about once every 3 months, more usually in the range from about once every 2 weeks up to about once every 10 weeks, e.g. once every 4 to 8 weeks. Antibody of the Invention is conveniently administered parenterally, intravenously, e.g. into the antecubital or other peripheral vein, intramuscularly, or subcutaneously. A prophylactic treatment typically comprises administering the Antibody of the Invention once per month to once every 2 to 3 months, or less frequently.

Pharmaceutical compositions of the invention may be manufactured in conventional manner. A composition according to the invention is preferably provided in lyophilized form. For immediate administration it is dissolved in a suitable aqueous carrier, for example sterile water for injection or sterile buffered physiological saline. If it is considered desirable to make up a solution of larger volume for administration by infusion rather as a bolus injection, it is advantageous to incorporate human serum albumin or the patient's own heparinised blood into the saline at the time of formulation. The presence of an excess of such physiologically inert protein prevents loss of antibody by adsorption onto the walls of the container and tubing used with the infusion solution. If albumin is used, a suitable concentration is from 0.5 to 4.5% by weight of the saline solution.

The invention is further described by way of illustration in the following Examples which refer to the accompanying Figure which shows dose response curves for the inhibition of IL-1β binding by soluble IL-1 receptors I and II.

EXAMPLES

Transgenic mice engineered to express the human IgG/κ repertoire instead of the murine immunoglobulin repertoire (Fishwild et al., 1996, Nat. Biotechnol., 14, 845-851) are used to generate antibodies to human IL-1β. B cells from these mice are immortalized by standard hybridoma technology and murine hybridoma cells are obtained which secrete the human IgG1/κ antibody ACZ 885

Example 1

Generation of the Hybridoma and Purification of the Antibody

Genetically engineered mouse 18077 (Medarex Inc. Annadale, N.J.) is immunized with recombinant human IL-1β coupled to KLH (50 µg) s.c. in several sites in adjuvant. The mouse is boosted five additional times with the last injection three days before the fusion. On the day of the fusion mouse 18077 is killed by $CO_2$ inhalation and spleen cells ($4.1 \times 10^7$) are fused by a routine method using PEG 4000 with an equal number of PAI-O cells, a mouse myeloma cell line. Fused cells are plated out in 624 wells (1 ml/well) containing a feeder layer of mouse peritoneal cells (Balb C mice), in HAT supplemented RPMI 1640, 10% heat inactivated fetal calf serum $5 \times 10^{-5}$ M β-mercaptoethanol. Supernatants are collected and tested in ELISA and screened for IL-1β reactive monoclonal antibodies. Five monoclonal antibodies of the IgG/κ subclass are identified. Cloning is done using 4×96 well microtiter plates, plating 0.5 cells per well. After two weeks wells are inspected with an inverted microscope. Supernatant is collected from wells positive for growth and production of anti-IL-1β monoclonal antibodies is evaluated by ELISA. 1-2L of conditioned supernatant from four subclones of the originally identified hybridoma #657 are prepared and antibodies are purified by affinity chromatography on a protein A column.

Purity and Partial Amino Acid Sequences of Heavy and Light Chain Amino Acid Sequencing Light and heavy chains of the purified antibody ACZ 885 are separated by SDS-PAGE and the amino-terminal amino acids determined by Edman degradation. The purity of the antibody used in these studies is ≧90% by sequencing. cDNA sequences coding for the heavy and light chain variable domains are obtained by PCR amplification of cDNA obtained from mRNA from the cloned hybridoma cells and fully sequenced. The amino-terminal sequences of heavy and light chain variable domains and the corresponding DNA sequences are given in SEQ ID NO:1 and SEQ ID NO:2.

Construction of Expression Vectors for Heavy and Light Chain

A GS based amplification/selection system such as that described in EP 0256055 B, EP 0323997 B or European patent application 89303964.4 is used, in which the selectable marker used is a GS coding sequence.

Example 2

Biochemical and Biological Data

The monoclonal antibody ACZ 885 is found to neutralize the activity of interleukin-1β in vitro. The monoclonal antibody is further characterized for its binding to recombinant human IL-1β Biacore analysis. The mode of neutralization is assessed by competitive binding studies with soluble IL-1 receptors. The biological activity of the antibody ACZ 885 towards recombinant and naturally produced IL-1β is determined in primary human cell (Example 3), responsive to stimulation by Determination of Dissociation Equilibrium Constant The association and dissociation rate constants for the binding of recombinant human IL-1beta to ACZ885 are determined by BIAcore analysis. ACZ885 is immobilized, and binding of recombinant IL-1beta in a concentration range from 1 to 4 nM is measured by surface plasmon resonance. The chosen format represents a monovalent interaction and thus permits treating the binding event of IL-1beta to ACZ885 according to a 1:1 stoichiometry. Data analysis is performed using the BIAevaluation software.

|  | $k_{on}$ [$10^5$/Ms] | $k_{off}$ [$10^{-5}$/s] | $K_D$ [pM] |  |
|---|---|---|---|---|
| Human IL-1β | 11.0 +/− 0.23 | 3.3 +/− 0.27 | 30.5 +/− 2.6 | n = 22 |

Conclusion: ACZ885 binds to recombinant human IL-1beta with very high affinity.

Binding Competition Study with Soluble IL-1 Type I and II Receptors

Competition between ACZ885 and soluble human IL-1 type I and type II receptors is measured by Biacore. ACZ885 is immobilized on the chip surface and recombinant human IL-beta (1 nM) is injected for binding to ACZ885 in absence or presence of increasing concentrations of recombinant human soluble receptor I or receptor II (0-12 nM; 4 independent runs each.). The results obtained are given in the accompanying Figure.

Binding of NVP-ACZ885 to human IL-1β was determined in the presence of recombinant human soluble IL-1 type I or type II receptors. Half-maximum values (IC50) were determined graphically using the Origin 6.0 software The mean±SEM is given (n=4).

Conclusion: Binding of ACZ885 to IL-1beta is competitive with both IL-1 receptor type I and type II.

Reactivity Profile to Human IL-1Alpha, Human IL-1RA, and IL-1Beta from Other Species The reactivity profile of ACZ885 to human IL-1alpha, IL-1RA, and cynomolgous, rabbit, murine and rat IL-1beta is determined by Biacore analysis. ACZ885 is immobilized, and the cytokines examined are applied at a concentration of 8 nM (6 independent runs.)

TABLE 3

Crossreactivity of NVP-ACZ885 with IL-1β, IL-1α, and IL-1Ra

|  |  | % Binding (mean +/− SEM) |
|---|---|---|
| Rec Human IL-1β | (n = 6) | 100 |
| Rec Cynomolgus IL-β | (n = 11) | 7.8 +/− 1.0 |
| Rec Rabbit IL-1β | (n = 6) | −0.5 +/− 0.2 |
| Rec Mouse IL-1β | (n = 6) | −2.6 +/− 0.6 |
| Rec Rat IL-1β | (n = 6) | −6.2 +/− 1.0 |
| Rec Human IL-1 α | (n = 6) | 8.4 +/− 2.4 |
| Rec Human IL-1Ra | (n = 6) | −3.7 +/− 1.7 |

Resonance units were read at 1000 s after injection start; an injection of running buffer was subtracted from all sensorgrams, and the baseline after immobilization of anti-Fcγ set to zero. Binding is expressed as percentage of accumulated resonance units for human IL-1β.

Conclusion: ACZ885 does not significantly crossreact with human IL-1 alpha, human IL-1RA, or cynomolgous, rabbit, murine or rat IL-1beta.

Example 3

Neutralization of the Release of IL-6 from Human Dermal Fibroblasts by ACZ885

The following methodology was used to assess the biological activity of ACZ885 in neutralizing the action of human IL-1β:
1. Preparation of Conditioned Medium Containing IL-1β
   The preparation of conditioned medium from human peripheral blood mononuclear cells was done as follows: mononuclear cells were prepared from the peripheral blood of monkeys using ficoll-hypaque density separation according to the method of Hansel [Hansel, T. T. et. al. (1991). An improved immunomagnetic procedure for the isolation of highly purified human blood eosinophils. J. Imm. Methods. 145: 105-110]; they were used at a concentration of $10^5$ cells/well in RPMI/10% FCS. IFNβ (100 U/ml) and LPS (5 μg/ml) were added and cells were subsequently incubated for 6 hrs. Incubation was terminated by centrifugation at 1200 RPM for 10 min. IL-1β in the supernatant was quantified using an ELISA
2. Neutralization Assay
   Human dermal foreskin fibroblasts were obtained from Clonetics (CC-2509) and grown in FBM (Clonetics, CC-3131) including bFGF (1 ng/ml, CC-4065), insulin (5 βg/ml, CC-4021), and 2% FCS(CC-4101).
   For induction of IL-6, cells were seeded at a density of $10^4$ cells per well in a 48 well tissue cluster. The following day, cells were starved for 6-7 h in FBM containing 2% FCS before addition of cytokine. For stimulation, the culture medium was replaced by FBM+2% FCS containing the appropriate amount of conditioned medium for about 50 pg/ml IL1β. Alternatively, recombinant human IL-1β at a final concentration of 50 pg/ml was used.
   Neutralizing anti-IL1β antibody was titrated into the diluted conditioned medium prior to addition to the cells. Recombinant IL-1Ra (R&D Systems #280-RA-010) was used as a positive control.
   Cell supernatant was taken 16-17 h after stimulation and the amount of released IL-6 determined in a sandwich ELISA.
3. IL-6 ELISA
   ELISA microtiter plates were coated with a murine anti-human IL-6 MAb (314-14 (Novartis Pharma; batch EN23,961, 5.5 mg/ml); 100 μl at 3 μg/ml) in PBS 0.02% NaN$_3$ and incubated overnight at +4° C. The following day, microtiter plates were washed 4 times with PBS/ 0.05% Tween/0.02% NaN$_3$ and blocked with 300 μl of PBS/3% bovine serum albumin (BSA)/0.02% NaN$_3$ for 3 h. Plates were washed again (4 times) and 100 μl of supernatant (final dilutions of 1:20) or of the recombinant human IL-6 standard ((Novartis Pharma #91902), titration curve ranging from 1 to 0.0156 ng/ml in 2 fold dilution steps) was added in duplicate. After an overnight incubation at RT the plates were washed (4 times) and a different murine anti-human IL-6 MAb (110-14, Novartis Pharma; 6.3 mg/ml); 100 μl at 1 μg/ml; 3 h at room temperature) was added. After additional 4 washes, a biotin-labelled goat anti-mouse IgG2b antiserum (Southern Biotechnology; #1090-08) was added at the final dilution of 1/10000 (100 μl/well; 3 h at room temperature). After incubation plates were washed 4 times and streptavidin coupled to alkaline phosphatase (Jackson Immunoresearch, #016-050-084) was added at a final dilution of 1/3000 (100 μl/well; 30 min at room temperature). After washing (4 times) the substrate (p-nitrophenylphosphate in diethanolamine buffer; 100 μl) was added for 30 min. Reaction was blocked by the addition of 50 μl/well of 1.5 M NaOH. Plates were read in a microtiter reader (Bio-Rad) using filters of 405 and 490 nm.
   IL-6 levels in culture supernatants were calculated in reference to the standard curve using the cubic curve fit. Statistical evaluation and determination of IC50 was performed based on sigmoidal curve fitting.

Results:

TABLE

Inhibition of IL-1β- induced IL-6 secretion

|  | NVP-ACZ885 Batch1 IC$_{50}$ [pM] ± SEM | NVP-ACZ885 Batch2 IC$_{50}$ [pM] ± SEM | IL-1ra IC$_{50}$ [pM] ± SEM |
|---|---|---|---|
| IL-6 secretion cond. medium | 54 ± 6.1 (9.1 ± 1.0 ng/ml) (n = 6) | 44.6 ± 3.6 (7.4 ± 0.6 ng/ml) (n = 6) | 30 ± 3.1 (0.51 ± 0.05 ng/ml) (n = 5) |
| IL-6 secretion rec. human IL-1β | 42 ± 3.4 (7.1 ± 0.56 ng/ml) (n = 4) | 63 ± 2.8 (10.5 ± 0.5) (n = 6) | nd |

IC$_{50}$ values for inhibition of IL-1β-induced secretion of IL-6 from human dermal fibroblasts. Fibroblasts were stimulated with recombinant human IL-1β or conditioned medium containing between 50 and 100 pg/ml of IL-1β.

Example 4

Definition of the Epitope for ACZ885

ACZ885 binds to human IL-1β with high affinity, but fails to recognize the highly homologous IL-1β derived from rhesus monkeys. One of the most prominent differences in the amino acid sequences between rhesus and human IL-1β is in position 64 of the mature IL-1β. Human IL-1β has a glutamic acid, and rhesus an alanine in this position. A mutant human IL-1β with the respective replacement Glu64Ala has lost its ability to bind to ACZ885 with measurable affinity. We conclude that Glu64 in human IL-1β is essential for recognition by the antibody ACZ885. Glu64 is located on a loop of IL-1β which is not part of the binding surface to the IL-1β type I receptor, or in close proximity to it. Thereby, antibodies directed against a binding epitope incorporating Glu64 have the potential to neutralize the biological activity of human IL-1β.

What is claimed is:

1. An isolated IL-1β antibody or antigen binding fragment thereof, comprising
   a) a heavy chain variable domain ($V_H$) comprising amino acids 20 to 137 of the amino acid sequence set forth as SEQ ID NO: 1;
   b) a light chain variable domain ($V_L$) comprising amino acids 20 to 126 of the amino acid sequence set forth as SEQ ID NO: 2;
   c) a $V_H$ comprising amino acids 20 to 137 of the amino acid sequence set forth as SEQ ID NO: 1 and a $V_L$ comprising amino acids 20 to 126 of the amino acid sequence set forth as SEQ ID NO: 2; or
   d) the three complementarity determining regions (CDRs) of a $V_H$ comprising amino acids 20 to 137 of the amino acid sequence set forth as SEQ ID NO: 1 and the three CDRs of a $V_L$ comprising amino acids 20 to 126 of the amino acid sequence set forth as SEQ ID NO: 2.

2. The isolated IL-1β antibody or antigen binding fragment thereof as set forth in claim 1, comprising:
   a) a heavy chain which comprises a $V_H$ comprising amino acids 20 to 137 of the amino acid sequence as set forth in SEQ ID NO:1 and the constant part of a human heavy chain; and
   b) a light chain which comprises a $V_L$ and the constant part of a human light chain.

3. The isolated IL-1β antibody or antigen binding fragment thereof as set forth in claim 1, comprising:
   a) a heavy chain which comprises a $V_H$ and the constant part of a human heavy chain; and
   b) a light chain which comprises a $V_L$ comprising amino acids 20 to 126 of the amino acid sequence set forth in SEQ ID NO:2 and the constant, part of a human light chain.

4. The isolated IL-1β antibody or antigen binding fragment thereof as set forth in claim 1, comprising:
 a) a heavy chain which comprises a $V_H$ comprising amino acids 20 to 137 of the amino add sequence as set forth in SEQ ID NO:1 and the constant part of a human heavy chain; and
 b) a light chain which comprises a $V_L$ comprising amino acids 20 to 126 of the amino acid sequence set forth in SEQ ID NO:2 and the constant part of a human light chain.

5. The isolated IL-1β antibody or antigen binding fragment thereof as set forth in claim 1, comprising:
 a) a heavy chain which comprises a $V_H$ comprising the three CDRs of the amino acid sequence as set forth in SEQ ID NO:1 and the constant part of a human heavy chain; and
 b) a light chain which comprises a $V_L$ comprising the three CDRs of the amino acid sequence set forth in SEQ ID NO:2 and the constant part of a human light chain.

6. The isolated IL-1β antibody or antigen binding fragment thereof as set forth in claim 1, wherein the three CDRs of a $V_H$ comprising amino acids 20 to 137 of the amino acid sequence set forth as SEQ ID NO:1 and the three CDRs of a $V_L$ comprising amino acids 20 to 126 of the amino acid sequence set forth as SEQ ID NO:2 are defined according to the Kabat definition.

7. The isolated IL-1β antibody or antigen binding fragment thereof as set forth in claim 1, wherein the three CDRs of a $V_H$ comprising amino acids 20 to 137 of the amino acid sequence set forth as SEQ ID NO:1 are the amino acid sequences set forth as SEQ ID NO:5, SEQ ID NO:6 and SEQ ID NO:7; and the three CDRs of a $V_L$ comprising amino acids 20 to 126 of the amino acid sequence set forth as SEQ ID NO:2 are the amino acid sequences set forth as SEQ ID NO:8, SEQ ID NO:9 and SEQ ID NO:10.

8. The isolated IL-1β antibody or antigen binding fragment thereof as set forth in claim 1, which is a F(ab')$_2$ fragment, a Fab fragment, a chimeric antibody, a CDR-grafted antibody, a human antibody, a single chain antibody or a single domain antibody.

9. The isolated IL-1β antibody or antigen binding fragment thereof as set forth in claim 1, which is a human antibody.

10. A pharmaceutical composition comprising the isolated IL-1β antibody or antigen binding fragment thereof as set forth in claim 1 and a pharmaceutically acceptable diluent, excipient, carrier or mixture thereof.

11. A method for treating an IL-1β mediated disease or disorder or an inflammatory disease or disorder in a subject in need thereof, comprising administering to the subject an effective amount of the isolated IL-1β antibody or antigen binding fragment thereof according to claim 1.

12. The method according to claim 11, wherein the IL-1β mediated disease or disorder or an inflammatory disease or disorder is arthritis.

13. A method for modulating IL-1β in a subject, comprising administering to the subject an effective amount of the isolated IL-1β antibody or antigen binding fragment thereof according to claim 1.

14. A method for administering an IL-1β inhibitor to a subject in need thereof, comprising administering to the subject an effective amount of the isolated IL-1β antibody or antigen binding fragment thereof according to claim 1.

\* \* \* \* \*

SEQUENCE LISTING

```
<160> NUMBER OF SEQ ID NOS: 10

<210> SEQ ID NO 1
<211> LENGTH: 137
<212> TYPE: PRT
<213> ORGANISM: homo sapiens

<400> SEQUENCE: 1

Met Glu Phe Gly Leu Ser Trp Val Phe Leu Val Ala Leu Leu Arg Gly
1               5                   10                  15

Val Gln Cys Gln Val Gln Leu Val Glu Ser Gly Gly Gly Val Val Gln
            20                  25                  30

Pro Gly Arg Ser Leu Arg Leu Ser Cys Ala Ala Ser Gly Phe Thr Phe
        35                  40                  45

Ser Val Tyr Gly Met Asn Trp Val Arg Gln Ala Pro Gly Lys Gly Leu
    50                  55                  60

Glu Trp Val Ala Ile Ile Trp Tyr Asp Gly Asp Asn Gln Tyr Tyr Ala
65                  70                  75                  80

Asp Ser Val Lys Gly Arg Phe Thr Ile Ser Arg Asp Asn Ser Lys Asn
                85                  90                  95

Thr Leu Tyr Leu Gln Met Asn Gly Leu Arg Ala Glu Asp Thr Ala Val
            100                 105                 110

Tyr Tyr Cys Ala Arg Asp Leu Arg Thr Gly Pro Phe Asp Tyr Trp Gly
        115                 120                 125

Gln Gly Thr Leu Val Thr Val Ser Ser
    130                 135

<210> SEQ ID NO 2
<211> LENGTH: 126
<212> TYPE: PRT
<213> ORGANISM: homo sapiens

<400> SEQUENCE: 2
```

```
Met Leu Pro Ser Gln Leu Ile Gly Phe Leu Leu Leu Trp Val Pro Ala
1               5                   10                  15

Ser Arg Gly Glu Ile Val Leu Thr Gln Ser Pro Asp Phe Gln Ser Val
            20                  25                  30

Thr Pro Lys Glu Lys Val Thr Ile Thr Cys Arg Ala Ser Gln Ser Ile
            35                  40                  45

Gly Ser Ser Leu His Trp Tyr Gln Gln Lys Pro Asp Gln Ser Pro Lys
        50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Ala Glu Asp Ala Ala Ala Tyr Tyr Cys His Gln Ser Ser Ser
            100                 105                 110

Leu Pro Phe Thr Phe Gly Pro Gly Thr Lys Val Asp Ile Lys
        115                 120                 125

<210> SEQ ID NO 3
<211> LENGTH: 410
<212> TYPE: DNA
<213> ORGANISM: homo sapiens

<400> SEQUENCE: 3
atggagtttg ggctgagctg ggttttcctc gttgctcttt taagaggtgt ccagtgtcag      60
gtgcagctgg tggagtctgg gggaggcgtg gtccagcctg gaggtccct  gagactctcc     120 tgtgcagcgt ctggattcac cttcagtgtt tatggcatga actgggtccg ccaggctcca    180
ggcaaggggc tggagtgggt ggcaattatt tggtatgatg agataatca  atactatgca    240 gactccgtga agggccgatt caccatctcc agagacaatt ccaagaacac gctgtatctg    300
caaatgaacg gcctgagagc cgaggacacg gctgtgtatt attgtgcgag agatcttagg    360
actgggcctt ttgactactg gggccaggga accctggtca ccgtctcctc              410

<210> SEQ ID NO 4
<211> LENGTH: 378
<212> TYPE: DNA
<213> ORGANISM: homo sapiens

<400> SEQUENCE: 4
atgttgccat cacaactcat tgggtttctg ctgctctggg ttccagcctc caggggtgaa      60
attgtgctga ctcagtctcc agactttcag tctgtgactc caaaggagaa agtcaccatc    120
acctgccggg ccagtcagag cattggtagt agcttacact ggtaccagca gaaaccagat    180
cagtctccaa agctcctcat caagtatgct tcccagtcct tctcagggt  cccctcgagg    240 ttcagtggca gtggatctgg gacagatttc accctcacca tcaatagcct ggaagctgaa    300
gatgctgcag cgtattactg tcatcagagt agtagtttac cattcacttt cggccctggg    360
accaaagtgg atatcaaa                                                  378

<210> SEQ ID NO 5
<211> LENGTH: 5
<212> TYPE: PRT
<213> ORGANISM: HOMO SAPIENS

<400> SEQUENCE: 5

Val Tyr Gly Met Asn
1               5
```

```
<210> SEQ ID NO 6
<211> LENGTH: 17
<212> TYPE: PRT
<213> ORGANISM: HOMO SAPIENS

<400> SEQUENCE: 6

Ile Ile Trp Tyr Asp Gly Asp Asn Gln Tyr Tyr Ala Asp Ser Val Lys
1               5                   10                  15
Gly

<210> SEQ ID NO 7
<211> LENGTH: 6
<212> TYPE: PRT
<213> ORGANISM: HOMO SAPIENS

<400> SEQUENCE: 7

Asp Leu Arg Thr Gly Pro
1               5

<210> SEQ ID NO 8
<211> LENGTH: 11
<212> TYPE: PRT
<213> ORGANISM: HOMO SAPIENS

<400> SEQUENCE: 8

Arg Ala Ser Gln Ser Ile Gly Ser Ser Leu His
1               5                   10

<210> SEQ ID NO 9
<211> LENGTH: 6
<212> TYPE: PRT
<213> ORGANISM: HOMO SAPIENS

<400> SEQUENCE: 9

Ala Ser Gln Ser Phe Ser
1               5

<210> SEQ ID NO 10
<211> LENGTH: 7
<212> TYPE: PRT
<213> ORGANISM: HOMO SAPIENS

<400> SEQUENCE: 10

His Gln Ser Ser Ser Leu Pro
1               5
```